US009272973B2

(12) United States Patent
Fridag et al.

(10) Patent No.: US 9,272,973 B2
(45) Date of Patent: Mar. 1, 2016

(54) STABLE LONG-TERM METHOD FOR PRODUCING C5-ALDEHYDES

(71) Applicants: Dirk Fridag, Haltern am See (DE); Robert Franke, Marl (DE); Dieter Hess, Marl (DE); Markus Schwarz, Haltern am See (DE); Katrin Marie Dyballa, Recklinghausen (DE); Hans-Gerd Lueken, Marl (DE); Bart Hamers, VG Horst (NL); Uwe Ernst, Marl (DE)

(72) Inventors: Dirk Fridag, Haltern am See (DE); Robert Franke, Marl (DE); Dieter Hess, Marl (DE); Markus Schwarz, Haltern am See (DE); Katrin Marie Dyballa, Recklinghausen (DE); Hans-Gerd Lueken, Marl (DE); Bart Hamers, VG Horst (NL); Uwe Ernst, Marl (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 14/435,052

(22) PCT Filed: Sep. 27, 2013

(86) PCT No.: PCT/EP2013/070208
§ 371 (c)(1),
(2) Date: Apr. 10, 2015

(87) PCT Pub. No.: WO2014/056732
PCT Pub. Date: Apr. 17, 2014

(65) Prior Publication Data
US 2015/0224488 A1     Aug. 13, 2015

(30) Foreign Application Priority Data

Oct. 12, 2012 (DE) .......................... 10 2012 218 625
Oct. 12, 2012 (DE) .......................... 10 2012 218 627
Oct. 12, 2012 (DE) .......................... 10 2012 218 629
Oct. 12, 2012 (DE) .......................... 10 2012 218 630

(51) Int. Cl.
| | |
|---|---|
| C07C 45/50 | (2006.01) |
| B01J 31/18 | (2006.01) |
| C07F 9/6574 | (2006.01) |
| B01J 31/02 | (2006.01) |
| B01J 19/24 | (2006.01) |
| C07C 67/38 | (2006.01) |
| C07F 9/6568 | (2006.01) |

(52) U.S. Cl.
CPC .............. *C07C 45/505* (2013.01); *B01J 19/24* (2013.01); *B01J 31/0209* (2013.01); *B01J 31/0237* (2013.01); *B01J 31/0271* (2013.01); *B01J 31/185* (2013.01); *C07C 45/50* (2013.01); *C07C 67/38* (2013.01); *C07F 9/65746* (2013.01); *B01J 2219/24* (2013.01); *B01J 2231/321* (2013.01); *B01J 2531/822* (2013.01); *C07F 9/65683* (2013.01); *C07F 9/65685* (2013.01)

(58) Field of Classification Search
CPC ........................................................ C07C 45/50
USPC ................................................. 568/454, 455
See application file for complete search history.

(56) References Cited

U.S. PATENT DOCUMENTS

| | | | |
|---|---|---|---|
| 6,482,992 B2 | 11/2002 | Scholz et al. |
| 6,500,991 B2 | 12/2002 | Wiese et al. |
| 6,960,699 B2 | 11/2005 | Tötsch et al. |
| 7,138,552 B2 | 11/2006 | Kaizik et al. |
| 7,154,012 B2 | 12/2006 | Lueken et al. |
| 7,179,947 B2 | 2/2007 | Lueken et al. |
| 7,193,116 B2 | 3/2007 | Moeller et al. |
| 7,232,931 B2 | 6/2007 | Toetsch et al. |
| 7,317,130 B2 | 1/2008 | Möller et al. |
| 8,129,571 B2 | 3/2012 | Lueken et al. |
| 8,138,379 B2 | 3/2012 | Lueken et al. |
| 8,226,829 B2 | 7/2012 | Wiese et al. |
| 8,404,902 B2 | 3/2013 | Kreidler et al. |
| 8,461,394 B2 | 6/2013 | Lueken et al. |
| 8,748,643 B2 | 6/2014 | Priske et al. |
| 8,884,070 B2 | 11/2014 | Franke et al. |
| 8,969,628 B2 | 3/2015 | Priske et al. |
| 2007/0135665 A1 | 6/2007 | Wiese et al. |
| 2009/0032465 A1 | 2/2009 | Baumgarten et al. |
| 2011/0130595 A1 | 6/2011 | Lueken et al. |
| 2012/0123079 A1 | 5/2012 | Ungerank et al. |
| 2012/0279922 A1 | 11/2012 | Haensel et al. |
| 2015/0018576 A1 | 1/2015 | Baumgarten et al. |

FOREIGN PATENT DOCUMENTS

| | | |
|---|---|---|
| EP | 2 280 920 B1 | 12/2011 |
| WO | WO 2014/056733 A1 | 4/2014 |
| WO | WO 2014/056735 A1 | 4/2014 |
| WO | WO 2014/056736 A1 | 4/2014 |
| WO | WO 2014/056737 A1 | 4/2014 |

OTHER PUBLICATIONS

U.S. Appl. No. 14/435,007, filed Apr. 10, 2015, Christiansen, et al.
U.S. Appl. No. 14/434,988, filed Apr. 10, 2015, Christiansen, et al.
U.S. Appl. No. 14/434,879, filed Apr. 10, 2015, Christiansen, et al.
U.S. Appl. No. 14/434,827, filed Apr. 10, 2015, Christiansen, et al.
U.S. Appl. No. 14/653,717, filed Jun. 18, 2015, Fridag, et al.
U.S. Appl. No. 14/435,052, filed Apr. 10, 2015, Fridag, et al.
International Search Report issued Jan. 7, 2014 in PCT/EP2013/070208.

*Primary Examiner* — Sikarl Witherspoon
(74) *Attorney, Agent, or Firm* — Oblon, McClelland, Maier & Neustadt, L.L.P.

(57) ABSTRACT

The invention relates to a process for preparing aldehydes having five carbon atoms, in which an input mixture containing 10% by weight to 50% by weight of linear butenes and less than 5% by weight of 1-butene is hydroformylated with synthesis gas in the presence of a catalyst system comprising rhodium and at least one bisphosphite ligand, wherein the hydroformylation is effected in a reactor from which, over an operating period, a cycle gas containing at least a portion of the products and unconverted reactants from the hydroformylation is continuously drawn off and partly condensed, and uncondensed components of the cycle gas are recycled into the reactor, and wherein, after the operating period has expired, the hydroformylation is stopped, the reactor is freed of reaction residues and the hydroformylation is restarted. It is based on the problem of making such a process more economically viable. The problem is solved by using a bisphosphite of the formula (1) and/or (2) as ligand, extending the operating period to more than 8000 h, and not separating solid reaction residues out of the reactor during the course of the operating period.

13 Claims, 6 Drawing Sheets

(State of the art)

(State of the art)

STABLE LONG-TERM METHOD FOR PRODUCING C5-ALDEHYDES

The invention relates to a process for preparing aldehydes having five carbon atoms, in which an input mixture containing 10% by weight to 50% by weight of linear butenes and less than 5% by weight of 1-butene is hydroformylated with synthesis gas in the presence of a catalyst system comprising rhodium and at least one bisphosphite ligand, wherein the hydroformylation is effected in a reactor from which, over an operating period, a cycle gas containing at least a portion of the products and unconverted reactants from the hydroformylation is continuously drawn off and partly condensed, and uncondensed components of the cycle gas are recycled into the reactor, and wherein, after the operating period has expired, the hydroformylation is stopped, the reactor is freed of reaction residues and the hydroformylation is restarted.

The aldehydes having five carbon atoms ($C_5$ aldehydes for short) include n-pentanal (valeraldehyde), isopentanal (isovaleraldehyde), sec-pentanal (2-methylbutanal) and tert-pentanal (pivalaldehyde).

Pentanals serve as starting materials for obtaining pentanols, pentanoic acids and pentylamines. Through aldol condensate and total hydrogenation of the aldol condensate, it is possible to obtain decanols therefrom, the latter being intermediates for the production of plasticizers, detergents and lubricants. Through the aldol condensation thereof, hydrogenation of the olefinic double bond of the aldol condensate and subsequent oxidation of the aldehydic group, it is possible to obtain decanoic acids which can be used, for example, for production of lubricants or detergents.

Pentanals can be obtained through hydroformylation of unsaturated compounds having four carbon atoms. Hydroformylation (the oxo process) is generally understood to mean the conversion of unsaturated compounds such as olefins (alkenes) in particular with synthesis gas (hydrogen and carbon monoxide) to aldehydes having a number of carbon atoms 1 higher than the number of carbon atoms in the starting compounds. $C_5$ aldehydes are accordingly prepared by hydroformylating $C_4$ olefins.

A good overview of the state of hydroformylation of olefins can be found in

B. Cornils, W. A. Herrmann, "Applied Homogeneous Catalysis with Organometallic Compounds", Vol. 1 & 2, VCH, Weinheim, N.Y., 1996 and in

R. Franke, D. Selent, A. Börner, "Applied Hydroformylation", Chem. Rev., 2012, DOI10.1021/cr3001803.

In industrial practice, the $C_4$ olefins, however, are not used as high-value pure substances but as crude mixtures containing different isomeric $C_4$ olefins. Since the individual $C_4$ olefins form different $C_5$ aldehydes in the hydroformylation, the hydroformylation of these $C_4$ mixtures also gives rise to a mixture of different $C_5$ aldehydes.

Specifically, in industrial pentanal preparation, $C_4$ hydrocarbon mixtures containing 1-butene, trans-2-butene, cis-2-butene and isobutene are used. As well as these $C_4$ olefins, it is also possible for olefins having more or fewer carbon atoms or alkanes (paraffins) to be present in the input mixture.

According to the position of the C—C double bond in the unsaturated $C_4$ compounds, and depending on the reaction conditions, the hydroformylation thereof affords linear and branched $C_5$ aldehydes or $C_5$ aldehyde mixtures in different selectivities.

If plasticizers or detergents are to be produced from the $C_5$ aldehyde mixture at a later stage, it is important that the pentanal mixture consists very substantially exclusively of the linear compound n-pentanal (valeraldehyde), or that the proportion of branched $C_5$ aldehydes, such as 2-methylbutanal in particular, is at a minimum.

Therefore, the aim is to optimize the hydroformylation in the direction of its most sought-after reaction product: valeraldehyde.

1-Butene can be hydroformylated in more than 90% selectivity to give n-pentanal. Catalysts used for this purpose are usually complexes of rhodium and monophosphines. A standard catalyst is, for example, a complex consisting of rhodium and triphenylphosphine. The reaction can be conducted in homogeneous phase, as described, for instance, EP0562451, or in heterogeneous phase, as described, for instance, in DE02627354.

The selective preparation of n-pentanal from 2-butenes or of mixtures thereof is much more difficult. DE10108474, DE10108475, DE10108476 and DE10225282 describe the preparation of $C_5$ aldehyde mixtures by hydroformylation of a mixture of linear butenes. A common factor in the technical teachings of all these documents is that a rhodium catalyst with a diphosphine ligand having a xanthene skeleton is used in at least one hydroformylation step. With this catalyst, it is possible to hydroformylate 2-butenes under isomerizing conditions. The ratio of n-pentanal to 2-methylbutanal is at best 85 to 15. Documents DE10108474 and DE10108475 describe processes in which the hydroformylation is effected in two stages. In the first hydroformylation stage, using a catalyst consisting of rhodium and a monophosphate as ligand, 1-butene is converted to n-pentanal in a selectivity of 90%. The unconverted butenes, principally 2-butenes, are converted in the second hydroformylation stage using the abovementioned rhodium/bisphosphine. Documents DE10108476 and DE10225282 describe one-stage hydroformylation processes.

Higher selectivities for n-pentanal in the hydroformylation of 2-butenes can be obtained when a catalyst consisting of rhodium and bulky aromatic bisphosphites is used, as described in EP0213639 for example. However, the selectivity decreases significantly with time.

DE102005042464 specifies catalyst systems for the hydroformylation of olefins, comprising a complex consisting of rhodium and an organophosphorus compound and a sterically hindered secondary amine. These catalyst systems are notable for a prolonged high level of stability. They can be used for the hydroformylation of olefins having three to sixteen carbon atoms. In the examples, only 1-octene was hydroformylated. This gave rise to mixtures of several $C_9$ aldehydes, but nothing is said about the isomer distribution thereof.

As well as the choice of catalyst system, the apparatus construction of the hydroformylation plant, or oxo plant for short, and the mode of operation thereof have a significant influence on the economic viability of the process.

One option for industrial implementation of hydroformylations on the industrial scale is the gas recycle process. In a gas recycle process (or stripping reactor process), the products of the hydroformylation are discharged from the reactor in gaseous form together with excess synthesis gas. A general outline of hydroformylation in a gas recycle process can be found in:

Van Leeuwen, Piet W. N. M. and Claver, Carmen (edit.): Rhodium Catalyzed Hydroformylation. Catalysis by Metal Complexes. Volume 22. Kluwer, 2000, pages 212 ff.

The advantage of an oxo plant that works by the gas recycle process is its simple apparatus construction. However, because of the comparatively low volatility of the $C_5$ aldehydes and especially of the high boilers formed in side reactions, gas recycle processes are regarded as unacceptable for pentanal preparation; cf. van Leeuwen, loc. cit.

Nevertheless, there have been attempts to prepare $C_5$ aldehydes from $C_4$ olefin mixtures in a cycle gas process:

Thus, EP0016285B2 describes a gas recycle process for preparation of valeraldehyde from a mixture containing 2.23% n-butane, 1.06% isobutane, 69.88% 1-butene, 10.06% cis-2-butene and 15.1% trans-2-butene. Since no high demands are made on the selectivity of the catalyst system, apparently because of the high proportion of 1-butene in the starting mixture, a comparatively simple triorganophosphine ligand is used in the catalyst complex. In this way, valeraldehyde can be produced on the industrial scale with a simple gas recycle plant. In the economic assessment of this process, however, it should be noted that 1-butene is a sought-after comonomer for the production of high-value plastics. Therefore, valeraldehyde is competing for raw materials with other products based on 1-butene. It is therefore economically desirable to prepare $C_5$ aldehyde mixtures rich in n-pentanal from $C_4$ olefin mixtures low in 1-butene.

A corresponding process of the type specified at the outset is known from EP2280920B1. The inventors proceed from this document as the closest prior art.

In the gas recycle hydroformylation practised in EP2280920B1 for preparation of valeraldehyde, a starting mixture containing 35% 2-butenes and only 1% 1-butene is used. The remainder is inert butane. The mixture, which is extremely low in 1-butene, is hydroformylated with the aid of a symmetric bisphosphite ligand which is stabilized through addition of a sterically hindered secondary amine. Isononyl benzoate is mentioned as a solvent.

With this catalyst system, butene conversions of 60% to 75% are achieved. The percentage distribution between n-pentanal and 2-methylbutanal, i.e. the n/iso selectivity, was 95% to 5%.

A disadvantage of this catalyst system is that it causes a precipitate on the wall of the gas recycle reactor after an operating time of about 1000 h. Analysis of the precipitate showed that it comprises phosphorus-containing conversion products of the bisphosphite ligand and the amine used.

This means that the ligand described in EP2280920B1, in spite of the amine used as a stabilizer, breaks down after only a relatively short operating time for an industrially practicable process, and so the conversion in the reaction falls.

U.S. Pat. No. 5,364,950, and also U.S. Pat. No. 5,763,677 and "Catalyst Separation, Recovery and Recycling", edited by D. J. Cole-Hamilton, R. P. Tooze, 2006, NL, pages 25-26, describe the formation of what are called "poisoning phosphites" as a secondary reaction or ligand degradation reaction. These "poisoning phosphites" form in the course of use of aryl phosphite-modified rhodium complexes during the hydroformylation reaction. In the course of ligand degradation here, an aryl group is exchanged for an alkyl group in the hydroformylation product.

As well as the formation of the unwanted "poisoning phosphites", the phosphite ligand can also be broken down in the course of a hydrolysis reaction by the water traces formed in aldehyde condensation. A consequence of these degradation reactions of the ligands is that the concentration of hydroformylation-active rhodium complex species decreases over the course of time.

In order to counter this, fresh catalyst has to be added continuously, which is of course associated with additional catalyst costs. Furthermore, the constant breakdown of the ligand leads gradually to the reactor becoming clogged, such that barely any cycle gas can be blown into the reactor. Therefore, the hydroformylation has to be stopped, the reactor has to be freed of reaction residues such as the precipitate in particular and charged with fresh catalyst, and the hydroformylation has to be restarted. From an economic point of view, this is indeed unacceptable if the operating time of the process is only 1000 h before the precipitate necessitates cleaning and fresh charging of the reactor.

To solve this problem, EP2280920B1 proposes continuous filtering in order to remove insoluble conversion products of the bisphosphite ligand from the reaction system. Although this measure prolongs the operating time, it does not make the costly addition of fresh catalyst unnecessary. Furthermore, the filter circuit entails additional apparatus complexity.

In view of all the above, it has not been possible to date to specify an economically convincing concept for preparation of $C_5$ aldehyde mixtures having a high valeraldehyde content from $C_4$ olefin mixtures having a low 1-butene content.

Accordingly, the problem addressed by the invention is that of making the process known from EP2280920B1 more economically viable.

Figure 1:
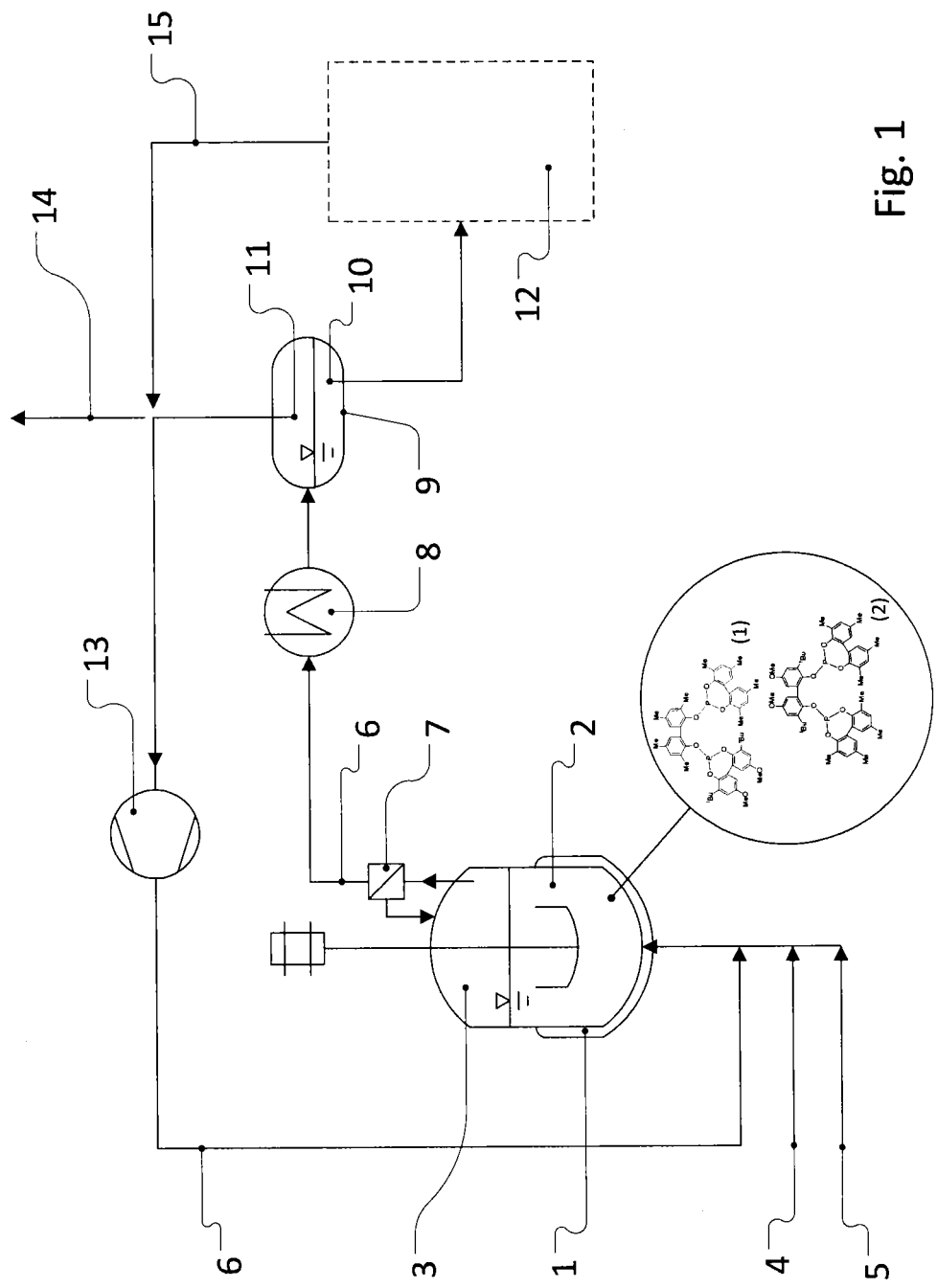
FIG. 1 is a schematic diagram illustrating an embodiment according to the invention.

The problem is solved by using, as ligand, a bisphosphite of the formula (1) and/or (2)

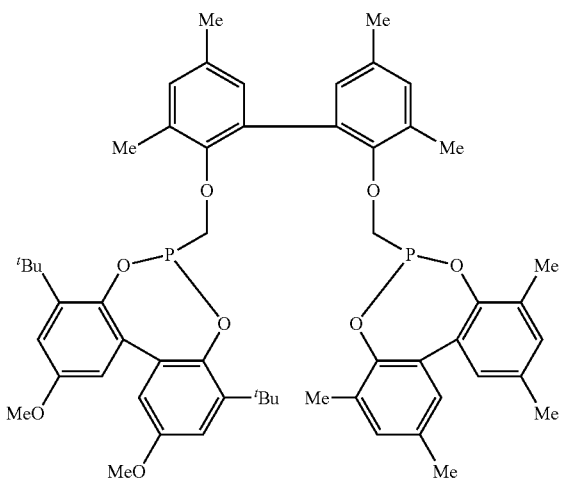

-continued

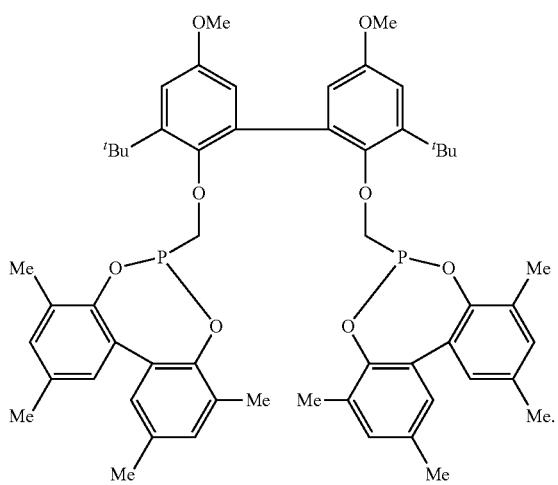

extending the operating period to more than 8000 h, and not separating solid reaction residues out of the reactor during the course of the operating period.

The invention relates to a process for preparing aldehydes having five carbon atoms, in which an input mixture containing 10% by weight to 50% by weight of linear butenes and less than 5% by weight of 1-butene is hydroformylated with synthesis gas in the presence of a catalyst system comprising rhodium and at least one bisphosphite ligand of the formula (1) and/or of the formula (2), wherein the hydroformylation is effected in a reactor from which, over an operating period lasting for at least 8000 h, a cycle gas containing at least a portion of the products and unconverted reactants from the hydroformylation is continuously drawn off and partly condensed, and uncondensed components of the cycle gas are recycled into the reactor, wherein, after the operating period has expired, the hydroformylation is stopped, the reactor is freed of reaction residues and the hydroformylation is restarted, and wherein there is no separation of solid reaction residues out of the reactor during the course of the operating period.

The invention is based on the finding that the ligand shown in the formulae (1) and (2) is broken down only slightly in the reaction system in question even over a long operating period of more than 8000 h, which is why the operating intervals between the cleaning and fresh charging of the reactor can be prolonged significantly without being reliant on a continuous separation of solid reaction residues. Surprisingly, the inventive catalyst system additionally achieves an n/iso selectivity which enables preparation of large amounts of n-valeraldehyde from input streams containing a much higher level of 2-butenes than 1-butene. The economic viability of the process according to the invention is therefore much higher than that of the process outlined in EP2280920B1.

The Rh-based catalyst system used in accordance with the invention includes the bisphosphite ligand of the formula (1) and/or the bisphosphite ligand of the formula (2). This means that either the unsymmetric ligand of the formula (1) or the symmetric ligand of the formula (2) is present in the catalyst system, or both ligands are present. More preferably, the catalyst system contains both ligands. The catalyst system need not contain any further ligands. Therefore, the ligands of the formulae (1) and (2) are preferably the only ligands present in the reaction system.

Incidentally, it is pointed out that free ligands can also occur in the reaction system, i.e. bisphosphites not coordinated to a rhodium nucleus. These free ligands are not catalytically active and therefore do not form part of the catalyst system in the context of the invention.

As already mentioned, preference is given to using a mixture of the bisphosphite ligands of the formula (1) and of the formula (2). However, it has been found that the unsymmetric bisphosphite ligand of the formula (1) is more catalytically active, more selective and more stable than its symmetric derivative of the formula (2). For this reason, the molar ratio of the bisphosphite ligands of the formula (1) to the bisphosphite ligands of the formula (2) should be between 10 and 20. This ratio relates to the hydroformylation as a whole. This means that 10 to 30 times the amount of ligand (1) is present in the reaction mixture, based on the total content of ligand (2). The calculation of this ratio includes not just the catalytically active species coordinated to rhodium but also the uncoordinated free ligands.

The molar ratio of rhodium to the sum total of the two bisphosphite ligands (1) and (2)—called the ligand/rhodium ratio—is preferably within a range from 1 to 100. This means that 1 to 100 bisphosphite ligands are counted for each rhodium nucleus. These values again apply to the reaction mixture as a whole. The ligand/rhodium ratio is especially in the range from 1 to 20, more preferably in the range from 1 to 2.

The concentration of rhodium in the reaction mixture is within a range from 1 to 1000 ppm by mass, especially within a range from 20 to 300 ppm by mass and very particularly in the range from 40 to 150 ppm by mass.

The catalyst system cannot be introduced into the process as an active complex ready for use, and instead has to be prepared in situ, i.e. in the reactor.

For this purpose, the active complex is prepared from stable, easily storable rhodium compounds in the presence of the bisphosphite ligands (1) and/or (2) within the hydroformylation reactor under hydroformylation conditions. Suitable rhodium compounds for this purpose are, for example, rhodium(II) and rhodium(III) salts such as rhodium(III) chloride, rhodium(III) nitrate, rhodium(III) sulphate, potassium rhodium sulphate, rhodium(II) or rhodium(III) carboxylate, rhodium(II) and rhodium(III) acetate, rhodium(II) octanoate, rhodium(II) nonanoate, rhodium(III) oxide, salts of rhodium (III) acid, trisammoniumhexachlororhodate(III). Also suitable are rhodium complexes such as rhodium biscarbonyl acetylacetonate, acetylacetonatobisethylenerhodium(I). Particularly suitable are rhodium acetate, rhodium octanoate and rhodium nonanoate.

In a preferred development of the invention, the hydroformylation is conducted in the presence of an organic amine of the formula (3).

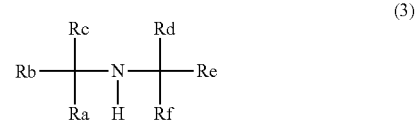

In formula (3), Ra, Rb, Rc, Rd, Re and Rf are identical or different hydrocarbyl radicals which may also be joined to one another.

This is because the organic amine prevents the hydrolysis of the bisphosphites used and therefore acts as a stabilizer.

The molar ratio of the entirety of the bisphosphites to the amine of the formula (3) is in the range from 0.1:10 to 10:1, especially within a range from 5:10 to 10:5 and very particularly within a range from 0.8:1 to 1:0.8.

More preferably, the organic amine has at least one 2,2,6,6-tetramethylpiperidine unit. Most preferably, the organic amine is a di-4-(2,2,6,6-tetramethylpiperidinyl) sebacate. The latter is available under the Tinuvin® brand name from BASF SE.

As well as the reactants, the catalyst system and the products, the reaction mixture may also contain an additional solvent for dissolving the catalyst system. Within the overall reaction mixture, the solvent may account for 60% to 80% by weight.

The solvent used is preferably isononyl benzoate. Isononyl benzoate (INB) is the ester of benzoic acid with isononanol. It is available from Evonik Industries AG under the Vestinol® INB brand name. It is classified under the CAS numbers 27458-94-2, 68515-81-1 or else 3452-97-9. It is generally prepared by esterification of isononanol with benzoic acid as described in DE10217186. The esterification and treatment conditions may also be varied, as described, for example, in U.S. Pat. No. 6,635,775 for other benzoic esters.

The advantage of the use of INB as solvent in the hydroformylation is that it has lower ecotoxicity compared to the aromatic solvents traditionally used.

The hydroformylation itself is conducted under customary reaction conditions, i.e. at a pressure between 1 and 20 MPa and at a temperature between 70° C. and 150° C.

The cycle gas should be partly condensed at a condensation temperature between 50° C. and 90° C. Preference is given to a range between 65° C. and 75° C.; very particular preference is given to partial condensation of the cycle gas at 70° C. The condensation of the cycle gas at this temperature is advantageous because a majority of the unconverted butenes and inert butane is not condensed in this way and can be fed back to the reaction via the cycle gas. However, the reaction products are condensed out for the most part and therefore do not lead to unwanted further reaction in the reactor.

According to the invention, the operating period over which the hydroformylation is operated continuously before it is stopped and the reactor is freed of reaction residues is 8000 hours. This corresponds to about one year of constant operation. However, the catalyst system used in accordance with the invention has such a prolonged high level of stability that the operating period may even be more than 12 000 hours. Only then is it necessary to stop the hydroformylation and free the reactor of reaction residues. The reaction residues include not just the catalyst system and its solid breakdown products but also any liquid by-products such as high boilers which, because of their volatility, are not discharged from the process continuously with the cycle gas.

"High boilers" in this context is a collective term for all the components of the reaction mixture having a higher boiling point than the solvent. The inventive catalyst system forms unwanted high boilers to such a minor degree that it is even possible to dispense with a separate apparatus for continuous high boiler discharge.

In the simplest case, the high boilers remain in the reactor until the scheduled operation stoppage and are then removed together with the catalyst residues during the shutdown. Because of its low formation of high boilers, it is the inventive catalyst system that makes the hydroformylation of $C_4$ olefins in a cycle gas process attractive, since barely any high-boiling by-products can be discharged with the cycle gas.

In the course of the operation stoppage, the reactor is restored to ambient pressure, completely emptied and cleaned. Thereafter, the hydroformylation is restarted by introducing the reactants and a fresh catalyst system.

The subsequent operating period may then again be 8000 or 12 000 hours or more.

A further advantage of the inventive catalyst system is also that it has a particularly high n/iso regioselectivity and is therefore able to process input mixtures containing a small proportion of 1-butene and therefore, as the substrate crucial for hydroformylation, predominantly the two other linear butenes cis-2-butene and trans-2-butene. Preferably, the input mixture contains 10% to 50% by weight of linear butenes, less than 2% by weight of 1-butene and at least 50% by weight of inert butanes. All the proportions by weight stated are based on the input mixture as a whole. The proportion of 1-butene specified separately is also based on the input mixture as a whole and not just on the fraction of linear butenes present therein.

The synthesis gas used preferably has a molar ratio of hydrogen to carbon monoxide within a range from 2:1 to 1:2, especially within a range from 1.1:0.9 to 0.9:1.1.

The invention also provides a plant for performance of the process according to the invention, comprising a reactor for preparation of aldehydes having five carbon atoms by hydroformylation of linear butenes and synthesis gas in the presence of a catalyst system comprising rhodium and at least one bisphosphite ligand, further comprising means for drawing off a cycle gas containing at least a portion of the products and unconverted reactants from the hydroformylation from the reactor, further comprising means for partial condensation of the cycle gas and for recycling of the uncondensed components of the cycle gas into the reactor. According to the invention, it is a feature of the plant that it contains at least one bisphosphite ligand of the formula (1) and/or (2) in its reactor.

Such an oxo plant for performance of the process according the invention is shown in schematic form in FIG. 1.

FIG. 1: Oxo plant for performance of the process (schematic).

The core of the plant is a reactor 1. The reactor 1 utilized may be any reactor design known in the prior art which is able to conduct gas/liquid reactions. More preferably, it is possible to use a bubble column or a stirred tank. The drawing shows a stirred tank reactor. Suitable bubble column reactors are described in Ullmann:

Deen, N. G., Mudde, R. F., Kuipers, J. A. M., Zehner, P. and Kraume, M.: Bubble Columns. Ullmann's Encyclopedia of Industrial Chemistry. Published Online: 15 Jan. 2010. DOI: 10.1002/14356007. b04_275.pub2

The "reactor" in this context may also be understood to mean a multitude of reactor vessels connected in series or in parallel.

The hydroformylation is a biphasic reaction comprising a liquid phase 2 and a gaseous phase 3. The individual components of the reaction mixture are distributed between the liquid phase 2 and the gaseous phase 3 according to their solubility and partial pressure. Only the catalyst system is dissolved exclusively in the liquid phase 2. Because of the complete dissolution of the catalyst system within the liquid phase 2, this is also referred to as a homogeneously catalysed reaction.

During the operating period, the reactants are introduced continuously into the reactor 1. The reactants used are the olefins which are present in an input mixture 4 and are introduced into the reactor 1. However, the olefins constitute a minor proportion in the input mixture 4, since the input mixture 4 consists of more than 50% butane. Butanes are inert within the hydroformylation and are flushed through the process unchanged. Only the olefins present in the input mixture 4 are hydroformylated.

The second reactant is synthesis gas 5, a mixture of carbon monoxide and hydrogen in approximately equal molar amounts.

Input mixture 4 and synthesis gas 5 are blown into the reactor 1 in gaseous form from the bottom, ascend through the liquid phase 2, and in the process react essentially to give valeraldehyde. In addition, there are side reactions which form unwanted by-products such as isovaleraldehyde, 2-methylbutanal and pivalaldehyde, and also high boilers having more than five carbon atoms. However, the proportion of by-product formation is low because of the high selectivity of the catalyst system used. Some of the aldehyde formed also reacts further with excess hydrogen to give alcohol, but here too only to a slight extent.

The $C_5$ products and unconverted reactants collect in the gas phase 3 within the reactor 1 and are drawn off from there as cycle gas 6. An aerosol breaker 7 prevents droplets of the liquid phase 2 from being entrained with the cycle gas 6. The droplets retained fall back into the reactor 1.

The cycle gas 6 is cooled down in a condenser 8 to a temperature of about 70° C., such that it partly condenses. In a phase separation vessel 9, the condensate 10 is separated from the uncondensed fraction 11 of the cycle gas.

The condensate 10 then contains essentially the target products of the process, the $C_5$ aldehydes; unwanted by-products such as high boilers are barely present. The condensate 10 is then fed to a workup 12 which is not shown here in detail, in which the condensate 10 is separated by distillation into its constituents. An extensive description of the workup of $C_5$ aldehyde mixtures can be found in EP2280920B1, and in DE102009027406A1. The workup 12 may be followed by an aldol condensation; cf. DE102009001594A1 and DE102009045139A1.

The uncondensed components of the cycle gas 11—essentially excess synthesis gas and $C_4$ hydrocarbons—are brought back to reaction pressure by a cycle gas compressor 13 and recycled into the reactor 1 together with fresh input mixture 4 and synthesis gas 5.

The uncondensed components 11 of the cycle gas need not be recycled in full. It is advisable to discharge a portion thereof from the process as offgas 14. The reason for this is that the uncondensed components 11 of the cycle gas, as well as synthesis gas and unconverted olefins, also contain inert alkanes such as the butane present in the input mixture 4. The inert butane is not consumed in the reaction and increases the power requirement of the cycle gas compressor 13. It therefore makes sense to discharge a portion of the uncondensed components 11 from the process as offgas 14. The offgas 14 is utilized either thermally or physically, for example by incineration or by recycling into a synthesis gas plant or a cracker.

Optionally, a recyclate 15 from the aldehyde workup 12 is added to the recycled cycle gas. This may, for example, be synthesis gas which was in dissolved form in the condensate and only outgassed in the course of the thermal workup 12.

According to the invention, the reactor 1 contains, dissolved in the liquid phase 2, a catalyst system comprising bisphosphite ligands of the formula (1) and/or (2); as shown in the detail enlargement. The ligands (1) and (2) coordinate to a rhodium nucleus to form the active species. Because of the high stability of these ligands, the inventive oxo plant does not need a continuous filtering operation, by means of which any breakdown products of the bisphosphite ligands would be separated out of the reaction system in the course of operation. The inventive oxo plant therefore has a construction which is simple in apparatus terms and reliable.

LIST OF REFERENCE NUMERALS 1 reactor
2 liquid phase
3 gaseous phase
4 input mixture
5 synthesis gas
6 cycle gas
7 aerosol breaker
8 condenser
9 phase separation vessel
10 condensate
11 uncondensed components of the cycle gas
12 workup
13 cycle gas compressor
14 offgas
15 recyclate

EXAMPLES

Example 1

Hydroformulation with the Noninventive Ligand (4) Over 1200 h

The noninventive ligand of the formula (4) known from EP2280920B1 was used in the hydroformylation of a butene/butane mixture.

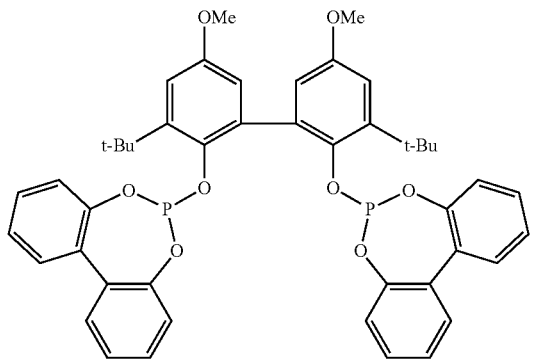 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

Ligand (4) was stabilized with the amine of the formula (5).

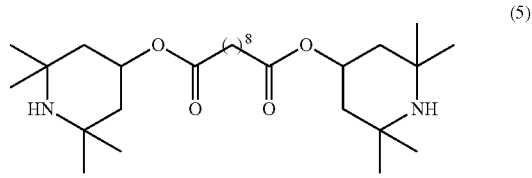

The continuously operated pilot plant consisted essentially of a pressure reactor of capacity 20 liters with a downstream condenser and phase separation vessel (gas/liquid) for the gas phase originating from the reactor, and a cycle gas compressor which returns the gas phase from the phase separation vessel back down into the reaction zone. A portion of this cycle gas is run out of the reaction system as offgas after the phase separation. In order to achieve optimal gas distribution in the reactor system, a gas distributor ring with bores was installed here. By means of installed heating and cooling apparatuses, the temperature of the reactor could be controlled.

Prior to the hydroformylation, the system was purged with nitrogen to free it of oxygen. Subsequently, the reactor was charged with 12 liters of catalyst solution.

This catalyst solution was composed of 12 kg of a eutectic mixture of biphenyl and diphenyl ether (Diphyl®, heat carrier oil from Lanxess), 3 g of Rh(acac)(CO)$_2$, 36 g of bisphosphite ligand of the formula (4), 67.5 g of amine of the formula (5), and was mixed beforehand in a vessel. The eutectic mixture of biphenyl and diphenyl ether (Diphyl®) was stripped with nitrogen beforehand, in order to remove oxygen and water from the heat carrier oil.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Then the addition of the starting materials was commenced. For this purpose, an input mixture was run through a vaporizer in order to run it into the cycle gas in gaseous form. The input mixture was a mixture of 35% by weight of 2-butenes and 1-butene in a concentration of about 1%. The rest was n-butane.

The following throughputs were set: 0.3 kg/h of input mixture, 75 l (STP)/h of synthesis gas (50% by vol. of H$_2$ and 50% by vol. of CO).

For the daily metered addition of the bisphosphite ligand (4) and amine (5), a 1.4% solution of the bisphosphite ligand (4) in n-pentanal, which had been freed of residual C$_4$ hydrocarbons (<3%) beforehand by stripping with nitrogen, was made up. The amine (5) was used in a threefold molar excess relative to the bisphosphite ligand (4). For better stabilization of this solution, the amine (5) was added to the solution before the bisphosphite ligand (4).

After about 1000 h, a steady state was attained. The reaction products were removed continuously from the reactor via the cycle gas stream and partially condensed out in a condenser at 50° C. The condensed phase was run continuously out of the phase separation vessel. To determine the conversion, samples were taken from the cycle gas upstream and downstream of the reactor.

By a daily metered addition of the above-described ligand solution, it was possible to keep the conversion and regioselectivity constant.

To determine the reactor contents, samples were taken from the reactor and analysed by means of liquid chromatography (HPLC). Under the selected reaction conditions, butene conversions of around 65 to 70% were achieved. The percentage distribution between n-pentanal and 2-methylbutanal, i.e. the n/iso selectivity, was 95% to 5%. In the steady-state phase of the experiment, no rhodium degradation was recorded.

Figure 2:
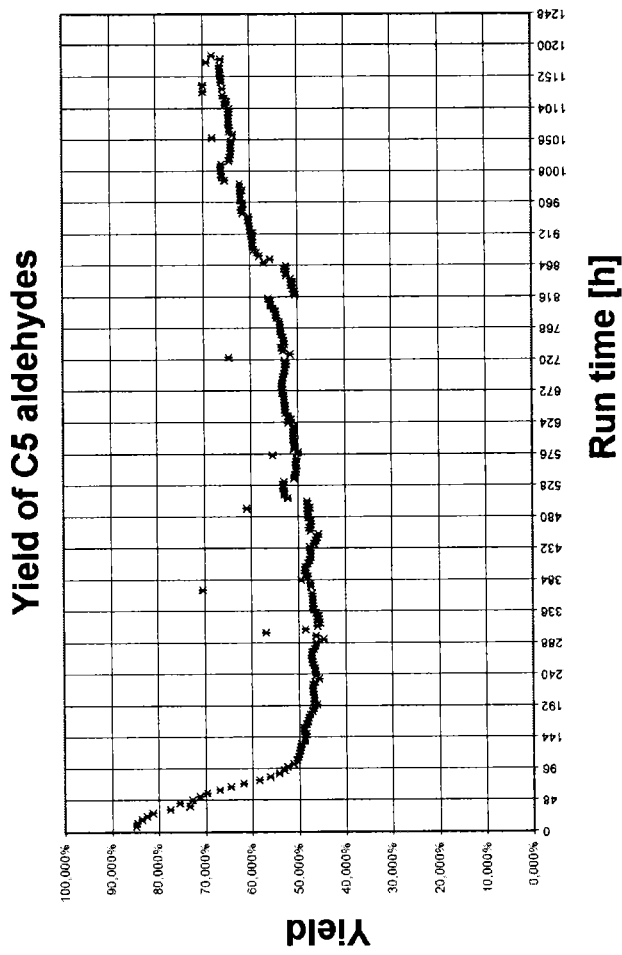
FIG. 2 is a graph showing pentanal yield versus run time for Example 1.

The yield of the C$_5$ aldehydes over the experiment duration is plotted in FIG. 2.

FIG. 2: Pentanal yield for Example 1

After 1200 h, the reactor was decompressed and the catalyst solution was analysed. A precipitate was found in the reactor. An analysis of this precipitate showed that it consisted of phosphorus-containing conversion products of the bisphosphite ligand (4) and the amine (5) used. No caking of these precipitated solids whatsoever was found in the reactor.

After removing the precipitate, a portion of the reactor contents was concentrated at 1.2 kPa abs. and bottom temperature 220° C. to 13% based on the starting material. The residue obtained from the liquid was still free-flowing, and no precipitate was found. A rhodium analysis showed that all the rhodium from the starting material was present in this liquid residue.

Example 2

Hydroformulation with the Noninventive Ligand (4) over 8000 h

The experiment was performed in the pilot plant described in Example 1. The preparation for the experiment and the procedure were analogous to Example 1.

In this example, the catalyst solution was composed of 12 kg of isononyl benzoate, 4.5 g of Rh(acac)(CO)$_2$, 55 g of bisphosphite ligand of the formula (4), 67.5 g of amine of the formula (5). The isononyl benzoate was likewise stripped beforehand with nitrogen, in order to remove oxygen and water from the solvent.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Subsequently, the addition of the starting materials was commenced. For this purpose, an input mixture was run through a vaporizer in order to run it into the cycle gas in gaseous form. The input mixture was a mixture of 35% by weight of 2-butenes and 1-butene in a concentration of about 1%. The rest was n-butane. The following throughputs were set: 0.3 kg/h of input mixture, 75 l (STP)/h of synthesis gas (50% by vol. of H$_2$ and 50% by vol. of CO).

For the daily metered addition of the bisphosphite ligand (4) and amine (5), a 1.4% solution of the bisphosphite ligand (4) in n-pentanal, which had been freed of residual C$_4$ hydrocarbons (<3%) beforehand by stripping with nitrogen, was made up. The amine (5) was used in a threefold molar excess relative to the bisphosphite ligand (4). For better stabilization of this solution, the amine (5) was added to the solution before the bisphosphite ligand (4).

As in Example 1, a steady state was attained after about 1000 h. The reaction products were removed continuously from the reactor via the cycle gas stream and partially condensed out in a condenser at 50° C. The condensed phase was run continuously out of the phase separation vessel. To determine the conversion, samples were taken from the cycle gas upstream and downstream of the reactor.

By a daily metered addition of the above-described ligand solution, it was possible to keep the conversion and regioselectivity constant.

To determine the reactor contents, samples were taken from the reactor and analysed by means of liquid chromatography (HPLC). Under the selected reaction conditions, butene conversions of around 65 to 70% were achieved. The percentage distribution between n-pentanal and 2-methylbutanal, i.e. the n/iso selectivity, was 95% to 5%. In the steady-state phase of the experiment, no rhodium degradation was recorded.

Figure 3:
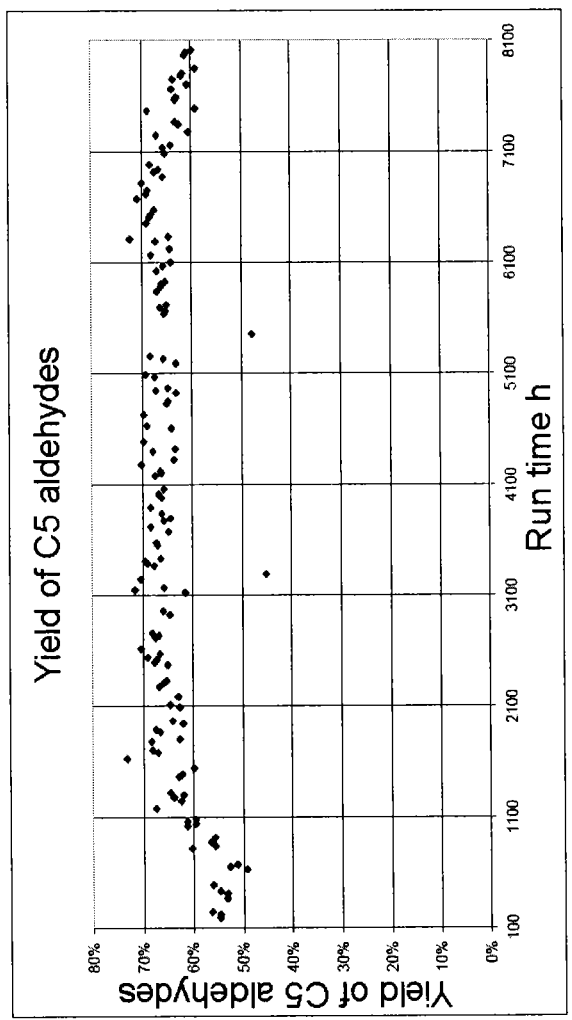
FIG. 3 is a graph showing pentanal yield versus run time for Example 2.

The yield of the $C_5$ aldehydes over the experiment duration is plotted in FIG. 3.

FIG. 3: Pentanal yield for Example 2

After 1500 h, the first precipitates were found in the samples from the reactor. The analysis of these precipitates showed that, just as in Example 1, they consisted of phosphorus-containing conversion products of the bisphosphite ligand (4) and the amine (5) used.

The reaction was conducted for a total of 8100 h; the rhodium losses through sampling were compensated for by addition of corresponding amounts of $Rh(acac)(CO)_2$ to the daily ligand metering solution.

As the reaction proceeded, after about 7000 h, a decline in activity was observed in the reaction and the reaction solution had a tendency to foam. It was no longer possible to operate the process, and the experiment had to be ended.

After the end of the reaction, the reactor was decompressed and the reaction mixture was analysed. Large amounts of solids were found. 250 ml of the reaction solution were stirred under an $N_2$ atmosphere at 40° C. for 4 h, and then the viscosity of the residue was measured. The viscosity was 300 mPas.

Example 3

Preparation of Ligands (1) and (2) Used in Accordance with the Invention

Figure 4:
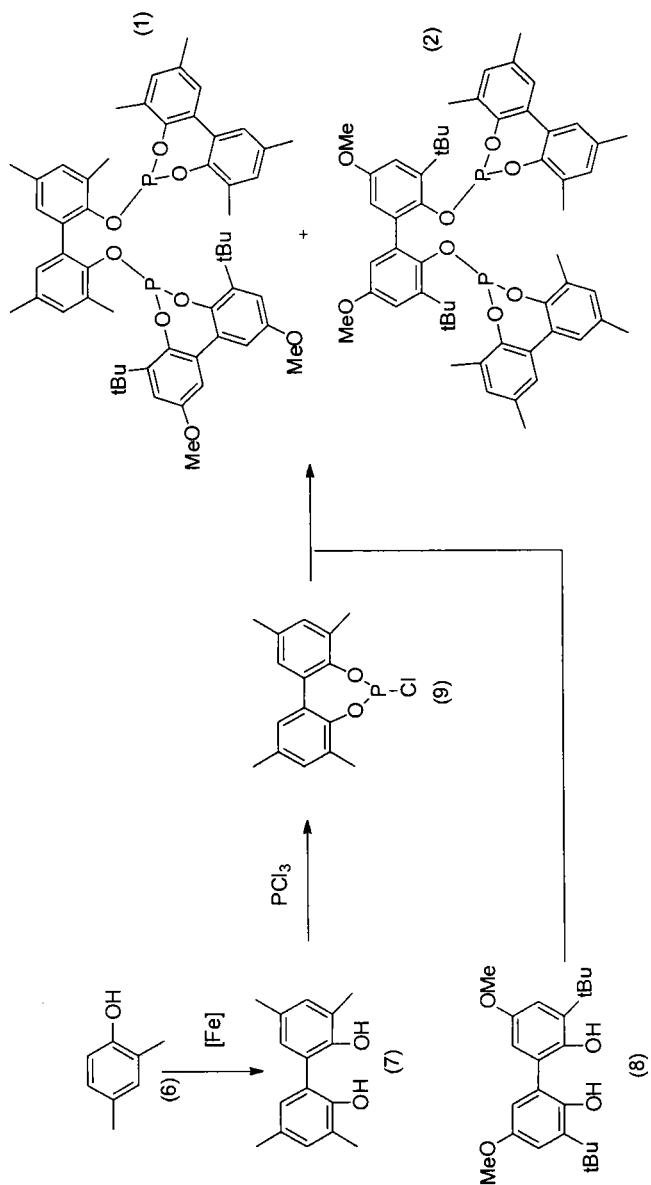
FIG. 4 is a schematic diagram illustrating a general reaction equation for preparation of a catalyst system according to an embodiment of the invention.

The general reaction equation for preparation of a catalyst system used in accordance with the invention is shown in FIG. 4:

FIG. 4: Preparation of inventive ligands

These abbreviations are used hereinafter:

DM water=demineralized water
CPG=core-pulled precision glass
ACN=acetonitrile
EtOAc=ethyl acetate
DMAB=dimethylaminobutane
NMP=N-methylpyrrolidone
OV=oil vacuum
acac=acetylacetonate
$NEt_3$=triethylamine
TIPB=1,2,4,5-tetraisopropylbenzene Synthesis of 2,2'-bis(3,5-dimethylphenol) of formula (7)

The biphenol (7) used as a precursor was prepared by the synthesis method which follows.

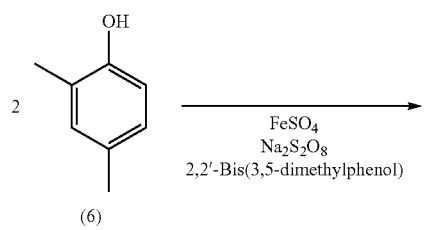

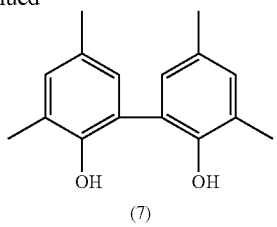

A 500 ml Schlenk with CPG stirrer, intermediate section and glass stirrer was initially charged with 1.42 g (0.005 mol) of iron(II) sulphate heptahydrate and 12.35 g (0.1 mol) of 2,4-dimethylphenol (6) in 150 ml of DM water and 5 ml of cyclohexane, and the mixture was heated to 40° C.

In a 100 ml beaker, 25.36 g (0.146 mol) of sodium peroxodisulphate were dissolved in 80 ml of DM water. At the start of the reaction, a small portion of $Na_2S_2O_8$ solution was added to the phenol. Subsequently, a smaller portion of the solution was added every 10 min. After 30 min, the $Na_2S_2O_8$ solution had been added.

After a reaction time of 5 h, 300 ml of cyclohexane and 200 ml of water were added to the reaction solution, which was left to stir for 20 min, then transferred while warm into a separating funnel.

The organic phase was removed and concentrated to dryness. The product was obtained in 69% yield (10.6 g).

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The product was characterized by NMR spectroscopy (Bruker Avance 500 MHz FT-NMR spectrometer). Chemical shifts (δ) are reported in ppm. The $^{31}P$ NMR signals were referenced according to: $SR_{31P}=SR_{1H}*(BF_{31P}/BF_{1H})= SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). By means of $^{31}P$ NMR, the ratio of the two ligands (ligand (1) and ligand (2)) to one another was determined. The unsymmetric ligand (1) is characterized by two phosphorus signals in the range from (δ)=140.6 ppm to (δ)=142.8 ppm, whereas the symmetric ligand (2) has only one phosphorus signal in the range from (δ)=139.1 ppm to (δ)=139.8 ppm.

Synthesis of 2,2'-bis(3,5-dimethylphenol) chlorophosphite (9)

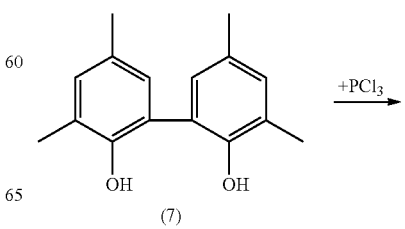

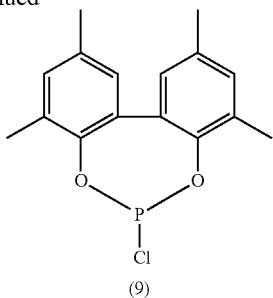

(9)

A 2 l Schlenk with magnetic stirrer which had been repeatedly evacuated and filled with inert gas was initially charged with 440 ml (692.56 g) of phosphorus trichloride. 120 g of 2,2'-bis(3,5-dimethylphenol) were weighed into a second 1 l Schlenk which had been repeatedly evacuated and filled with inert gas, and 500 ml of dried toluene were added while stirring. The biphenol-toluene suspension was metered into the phosphorus trichloride over 4 h at 63° C. On completion of the addition, the reaction mixture was stirred overnight at temperature. The next morning, the solution was concentrated while warm (45° C.) and the product was obtained in 96.5% yield (153 g). $^{31}$P NMR: 175.59 (94.8% 2,2'-bis(3,5-dimethylphenol) chlorophosphite), 4.4% various PCl compounds, 0.8% P—H compound.

Preparation of the Isomer Mixture Consisting of the Ligands (1) and (2):

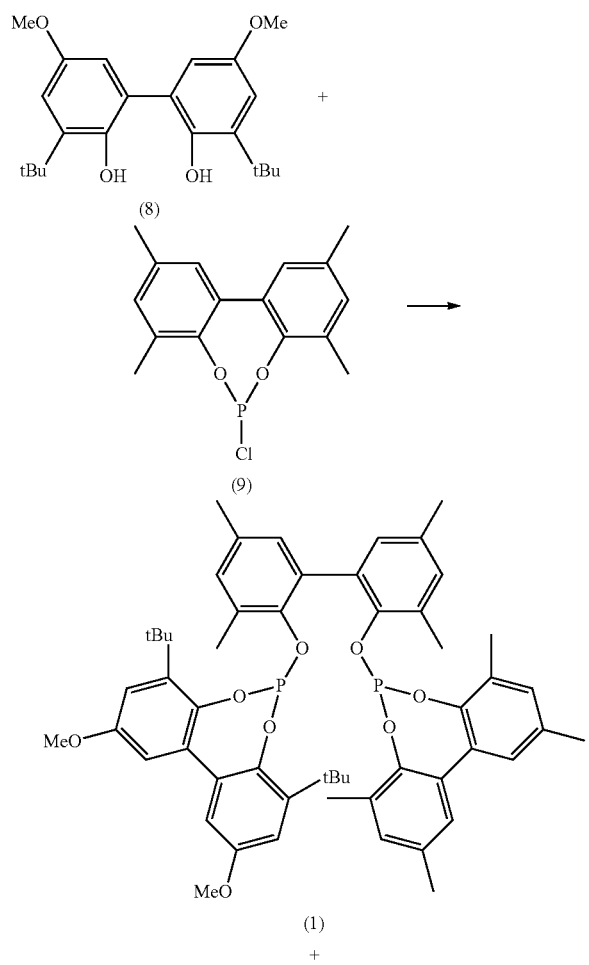

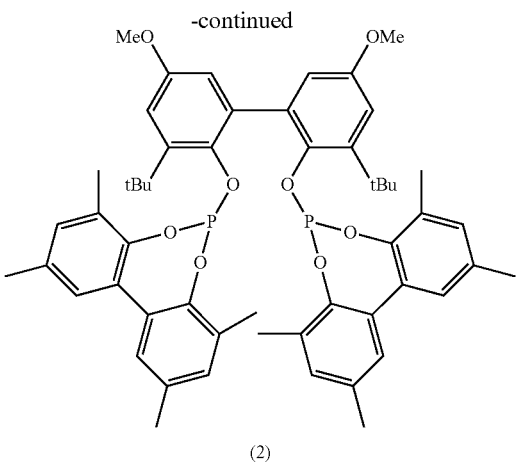

(2)

In a 1000 ml Schlenk, under protective gas, 38.75 g (0.121 mol) of 2,2'-bis(3,5-dimethylphenyl) chlorophosphite were dissolved in 150 ml of degassed ACN and heated to 35° C. In a second Schlenk (500 ml), 20.1 g (0.056 mol) of 3,3'-di-tert-butyl-5,5'-dimethoxy-[1,1'-biphenyl]-2,2'-diol were dissolved in 150 ml of degassed ACN, and 40.9 ml of degassed triethylamine (0.29 mol) were added while stirring. Then the biphenol/triethylamine solution was slowly added dropwise to the chlorophosphite solution. After a further reaction time of 1 h, the reaction solution was stirred overnight at 45° C.

Subsequently, the solution was filtered and the solids were washed three times with 100 ml of warm (45° C.) ACN. The target product was obtained as a white solid (43.3 g, 86%). 31P NMR (202.4 MHz, toluene-d8): 142.5 and 140.9 (95.4%), 139.2 (4.6%).

Example 4

Hydroformylation with Inventive Catalyst System

The same pilot plant was used as in Example 1. The same input mixture and the same synthesis gas were used. However, the ligand used was a mixture of the two bisphosphite ligands (1) and (2), which was prepared according to Example 3. The ligand of the formula (4) known from EP2280920B1 was not present in the reaction mixture. The same amine (5) as in Comparative Example 1 was used as a stabilizer. The solvent used was isononyl benzoate.

Prior to the hydroformylation, the system was purged with nitrogen to free it of oxygen. Subsequently, the reactor was charged with 12 liters of catalyst solution.

This catalyst solution was composed of 12 kg of isononyl benzoate, 4.5 g of Rh(acac)(CO)2, 63 g of ligand isomer mixture of the formulae (1) and (2), 200 g of amine of the formula (5), and was mixed beforehand in a vessel. The isononyl benzoate was stripped beforehand with nitrogen, in order to remove oxygen and water from the solvent.

Subsequently, the reactor system was purged with synthesis gas to free it of nitrogen. Once the nitrogen content had fallen below 10% by volume, the reactor system was pressurized to 1.0 MPa with synthesis gas and then heated to 120° C. On attainment of the operating temperature, the reactor system was brought to reaction pressure 1.7 MPa with synthesis gas.

Then the addition of the starting materials was commenced. The input mixture was run through a vaporizer in order to run it into the cycle gas in gaseous form. The following throughputs were set: 0.3 kg/h of input mixture, 75 l (STP)/h of synthesis gas.

For the daily metered addition of the isomer mixture consisting of (1) and (2) and amine (5), a 1.4% solution of the ligand mixtures of the bisphosphite ligands (1) and (2) in n-pentanal, which had been freed of residual $C_4$ hydrocarbons (<3%) beforehand by stripping with nitrogen, was made up. The amine (5) was used in a threefold molar excess relative to the ligand isomer mixture consisting of (1) and (2). For better stabilization of this solution, the amine (5) was added to the solution before the bisphosphite ligand isomer mixture.

The reaction products were removed continuously from the reactor via the cycle gas stream and partially condensed out in a condenser at 50° C. The condensed phase was run continuously out of the phase separation vessel. To determine the yield, samples were taken from the cycle gas upstream and downstream of the reactor and analysed by means of a gas chromatograph.

By a daily metered addition of the above-described ligand solution, it was possible to keep the conversion and regioselectivity constant. To determine the reactor contents, samples were taken from the reactor and analysed by means of liquid chromatography (HPLC).

Under the selected reaction conditions, an aldehyde yield between 80% and 90% was established at the start of the reaction. After an operating time of 8000 h, the yield fell to about 65%, caused by the rhodium losses resulting from the sampling. In this case, no foaming of the reaction solution was detectable. The percentage distribution between n-pentanal and 2-methylbutanal, i.e. the regioselectivity, was 92% to 8%.

Figure 5:
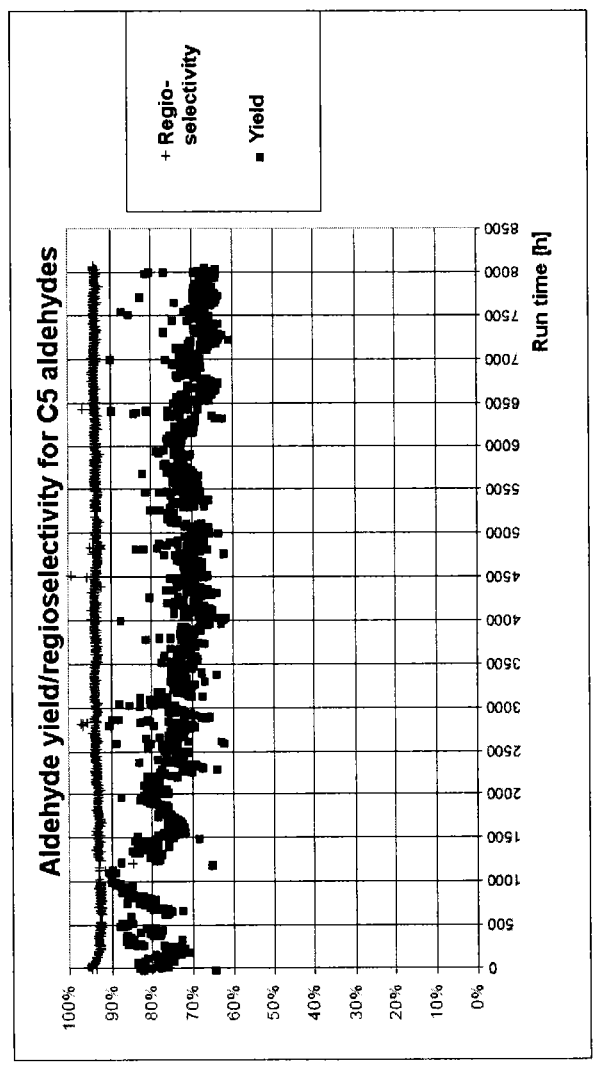
FIG. 5 is a graph showing aldehyde yield and regioselectivity versus run time for Example 4

Aldehyde yield and regioselectivity are plotted over the experiment duration in FIG. 5.

FIG. 5: Aldehyde yield and regioselectivity for Example 4

In the steady-state phase of the experiment, apart from the rhodium losses resulting from the sampling, no further rhodium degradation was recorded.

Figure 6:
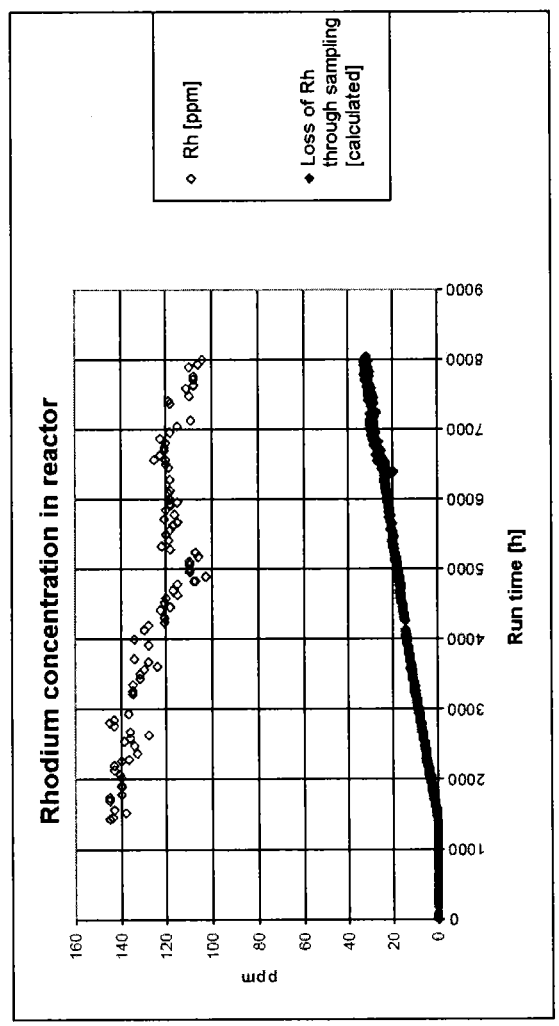
FIG. 6 is a graph showing rhodium concentration in a reactor versus run time for Example 4.

The rhodium concentration in the reactor over the experiment duration is plotted in FIG. 6.

FIG. 6: Rh concentration for Example 4

After the end of the reaction, the reactor was decompressed and the reaction mixture was analysed. No solids were found. 250 ml of the reaction solution were stirred under an $N_2$ atmosphere at 40° C. for 4 h, and then the viscosity of the residue was measured. The viscosity was 20 mPas.

Comparison of Examples 1, 2 and 4

Comparing the corresponding examples, Example 4 which was conducted in accordance with the invention is clearly set apart from Examples 1 and 2, which represent the prior art, by the following features:

Inventive Example 4 does not exhibit any run-in phase, meaning that the system does not show any decline in activity in the first 1000 h of operating time, and hence the plant in the inventive example produces much more product in the same period.

In Comparative Example 2, solids occur in the course of the reaction, which can be removed only via an inconvenient filtration. Inventive Example 4 shows no occurrence of solids even after more than 8000 h, and so it is possible to dispense with the filtration in this process.

Comparative Example 2 shows distinct foaming of the reaction solution at the end of the experiment, such that the process can no longer be operated. Such behaviour could only be prevented by inconvenient foam breakers. The process according to the invention does not need these aids.

The invention claimed is:

1. A process comprising preparing aldehydes having five carbon atoms, in which an input mixture comprising 10% by weight to 50% by weight of linear butenes and less than 5% by weight of 1-butene is hydroformylated with synthesis gas in the presence of a catalyst system comprising rhodium and at least one bisphosphite ligand, wherein the hydroformylation is effected in a reactor from which, over an operating period, a cycle gas comprising at least a portion of products and unconverted reactants from the hydroformylation is continuously drawn off and partly condensed, and uncondensed components of the cycle gas are recycled into the reactor, and wherein, after the operating period has expired, the hydroformylation is stopped, the reactor is freed of reaction residues and the hydroformylation is restarted, wherein the operating period lasts for at least 8000 h, there is no separation of solid reaction residues out of the reactor during the course of the operating period, and the catalyst system comprises the bisphosphite ligand of formula (1) and/or the bisphosphite ligand of formula (2):

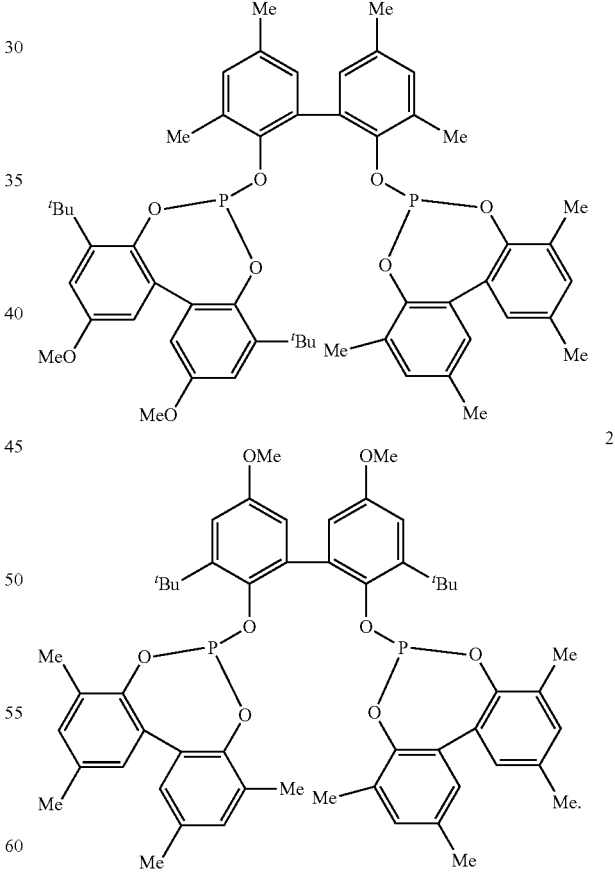

2. The process according to claim 1, wherein the catalyst system comprises both the bisphosphite ligand of the formula (1) and the bisphosphite ligand of the formula (2).

3. The process according to claim 2,
wherein
the molar ratio of the bisphosphite ligands of the formula (1) to the bisphosphite ligands of the formula (2) in the hydroformylation is between 10 and 30.

4. The process according to any of claim 1 or 2,
wherein
the hydroformylation is conducted in the presence of an organic amine of formula (3):

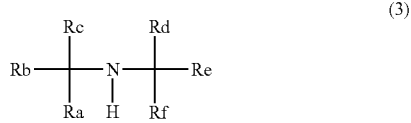

in which Ra, Rb, Rc, Rd, Re and Rf are identical or different hydrocarbyl radicals which may also be joined to one another.

5. The process according to claim 4,
wherein
the organic amine has at least one 2,2,6,6-tetramethylpiperidine unit.

6. The process according to claim 5,
wherein the organic amine is a di-4-(2,2,6,6-tetramethylpiperidinyl) sebacate.

7. The process according to claim 1,
wherein
the hydroformylation is conducted in the presence of isononyl benzoate.

8. The process according to claim 1,
wherein
the cycle gas is partly condensed at a condensation temperature of 50° C. to 90° C.

9. The process according to claim 1,
wherein
the operating period is 12 000 h or more.

10. The process according to claim 1,
wherein
the input mixture comprises 10% to 50% by weight of linear butenes, less than 2% by weight of 1-butene and at least 50% by weight of butanes.

11. The process according to claim 1,
wherein
the hydroformylation is conducted under the following reaction conditions:
Pressure: 1 MPa to 20 MPa;
Temperature: 70° C. to 150° C.;
Rhodium concentration: 1 ppm by weight to 1000 ppm by weight;
Ligand/rhodium ratio: 1 to 100.

12. The process according to claim 8, wherein the condensation temperature is between 65° C. and 75° C.

13. The process according to claim 8, wherein the condensation temperature is 70° C.

* * * * *